United States Patent
Li et al.

(10) Patent No.: US 11,085,863 B2
(45) Date of Patent: Aug. 10, 2021

(54) REAL-TIME ONLINE MONITORING AND SOURCE APPORTIONMENT METHOD FOR ATMOSPHERIC FINE PARTICLES CONTAINING HEAVY METALS

(71) Applicant: JINAN UNIVERSITY, Guangzhou (CN)

(72) Inventors: Mei Li, Guangzhou (CN); Mengxi Wu, Guangzhou (CN); Chunlei Cheng, Guangzhou (CN)

(73) Assignee: Jinan University, Guangzhou (CN)

( * ) Notice: Subject to any disclaimer, the term of this patent is extended or adjusted under 35 U.S.C. 154(b) by 0 days.

(21) Appl. No.: 17/168,601

(22) Filed: Feb. 5, 2021

(65) Prior Publication Data

US 2021/0156781 A1    May 27, 2021

Related U.S. Application Data

(63) Continuation of application No. PCT/CN2020/086607, filed on Apr. 24, 2020.

(30) Foreign Application Priority Data

Apr. 28, 2019 (CN) .......................... 201910349577.6

(51) Int. Cl.
  *G01N 15/02* (2006.01)
  *G01N 33/00* (2006.01)
  *G01N 15/06* (2006.01)

(52) U.S. Cl.
  CPC ............. *G01N 15/02* (2013.01); *G01N 15/06* (2013.01); *G01N 33/0036* (2013.01)

(58) Field of Classification Search
  CPC ........ G01N 15/00; G01N 15/02; G01N 15/06; G01N 1/22
  See application file for complete search history.

(56) References Cited

FOREIGN PATENT DOCUMENTS

| CN | 103674789 A | * | 3/2014 |
| CN | 103674789 A |   | 3/2014 |

(Continued)

OTHER PUBLICATIONS

Zhou Jing-bo et al., SPAMS, Characteristics and Formation Mechanism of a Multi-Day Haze in the Winter of Shijiazhuang Using a Single Particle Aerosol Mass Spectrometer, Environmental Science, Nov. 30, 2015., vol. 36 No. 11, Shijiazhuang CN.

(Continued)

*Primary Examiner* — Jennifer Wecker
(74) *Attorney, Agent, or Firm* — Thomas | Horstemeyer LLP

(57) ABSTRACT

The present disclosure provides an online monitoring and source apportionment method for atmospheric particles containing heavy metals, and belongs to the technical field of online quantification and source tracing of atmospheric particles containing heavy metals. The single particle aerosol mass spectrometer and X-ray fluorescence spectrometer are combined to quickly determine the concentration, time series, chemical compositions and mixing state of atmospheric particles containing heavy metals from both qualitative and quantitative perspectives. A heavy metal-containing particle mass concentration limit system is incorporated into the X-ray fluorescence spectrometer. Once the mass concentration of a particle containing heavy metals exceeds the standard, the aerosol mass spectrometer can immediately receive this alert through the information transmission system. The online source tracing system of aerosol mass spectrometer will start immediately after receiving the signal of the heavy metal exceeding the standard.

7 Claims, 1 Drawing Sheet

(56) References Cited

FOREIGN PATENT DOCUMENTS

| | | |
|---|---|---|
| CN | 105136631 A | 12/2015 |
| CN | 108414610 A | 8/2018 |
| CN | 110044779 A | 7/2019 |

OTHER PUBLICATIONS

Rao Zhi-han et al . . . , Source Apportionment of Particulate Matter in Cities of Sichuan Basin by Using Single Particle Aerosol Mass Spectrometer, Sichuan Environment, Dec. 31, 2018., vol. 37 No. 6, Chengdu CN.
Zhang Linlin et al., Comparative study on the characterization of air particulate matters based on SPAMS and off-line filter analyses, Environmental Chemistry, Nov. 30, 2018., vol. 37 No. 11, Beijing CN.
Yu Yi-yong., Progresses and Perspectives of On-line Source Apportionment of PM, Jun. 2015., vol. 27-3, Jiangsu CN.
Gallavardin S. et al., Analysis and differentiation of mineral dust by single particle laser mass spectrometry, International Journal of Mass Spectrometry, May 9, 2008., pp. 56-63, vol. 274, Zurich CH.
International Search Report for PCT/CN2020/086607 dated Jul. 22, 2020.

\* cited by examiner

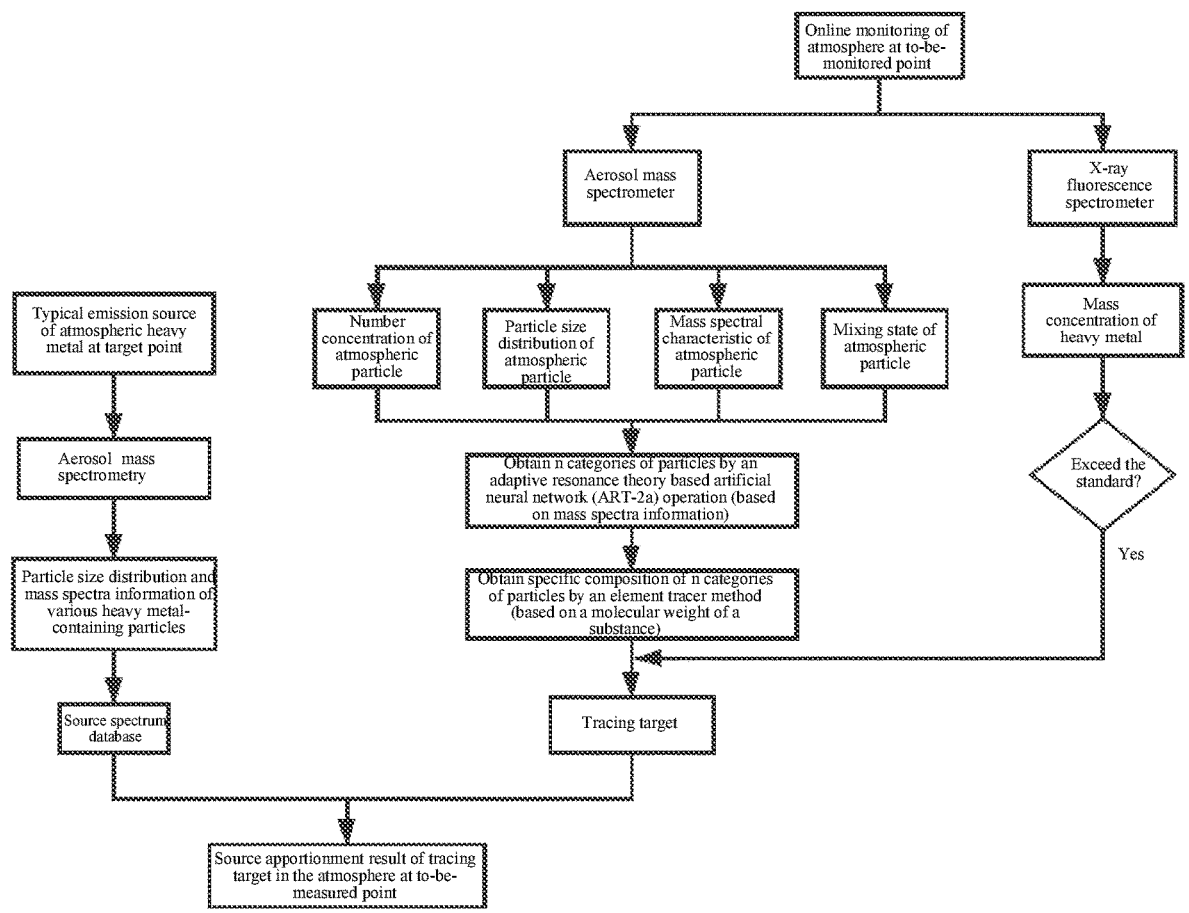

REAL-TIME ONLINE MONITORING AND SOURCE APPORTIONMENT METHOD FOR ATMOSPHERIC FINE PARTICLES CONTAINING HEAVY METALS

This application is a bypass continuation of International Application No. PCT/CN2020/086607, filed on Apr. 24, 2020, which claims priority to Chinese Patent Application No. 201910349577.6, filed with the China National Intellectual Property Administration (CNIPA) on Apr. 28, 2019 and entitled "REAL-TIME ONLINE MONITORING AND SOURCE APPORTIONMENT METHOD FOR ATMOSPHERIC FINE PARTICLES CONTAINING HEAVY METALS", both of which are incorporated herein by reference in their entirety.

TECHNICAL FIELD

The present disclosure relates to the technical field of online quantification and source tracing of atmospheric heavy metals, and particularly relates to a real-time online monitoring and source apportionment method for atmospheric fine particles containing heavy metals.

BACKGROUND

With the rapid development of social economy and the acceleration of industrialization and urbanization, atmospheric pollutants containing heavy metals enter the ambient atmosphere through various ways. Atmospheric heavy metal pollution has become one of the serious environmental pollutions which impact the world's environment and development. Its main pollution sources come from fossil fuel combustion, metal smelting, machining, mining, printing and dyeing, pesticides and brake wear, etc. Comprehensive monitoring of extremely harmful heavy metals and metalloids such as lead, mercury, cadmium, chromium and copper has an important practical significance for directly judging the harm of ambient air to human health, evaluating the quality of the urban atmospheric environment, and formulating prevention and control measures.

At present, the general analytical methods for atmospheric fine particles containing heavy metals are laboratory sampling analysis, such as inductively coupled plasma mass spectrometry, atomic absorption spectrometry, atomic fluorescence spectrometry, inductively coupled plasma atomic emission spectrometry, neutron activation analysis, and spark source mass spectrometry. These analytical methods require a series of processes including sampling, sample preparation, and testing, etc., and often take hours or even days to obtain a detection result. Such interval sampling methods can only reflect the content of a particle containing heavy metals in the atmosphere in a short period of time, and the sampling and processing will make it deviate from the actual sample condition and cause a detection error. Therefore, the traditional source apportionment methods have problems such as tedious sampling procedures, high apportionment components, and low time resolution. In addition, due to the limited amount of data obtained, the traditional methods have a certain limitation in the range of application. As people pay more and more attention to environmental quality, technologies and methods for real-time fast monitoring of heavy metals in the atmosphere have become a new trend.

SUMMARY

In view of this, an objective of the present disclosure is to provide an online monitoring and source apportionment method for atmospheric particles containing heavy metals, and the method provided by the present disclosure can not only obtain the information of a heavy metal exceeding the standard in a certain period of time more quickly and effortlessly, but also apportion a source of the heavy metal exceeding the standard in the atmosphere, which has an important significance and good industrial application prospect.

To achieve the above purpose, the present disclosure provides the following technical solutions:

The present disclosure provides an online monitoring and source apportionment method for atmospheric fine particles containing heavy metals, including the following steps:

(1) determining a typical emission source of an atmospheric heavy metal at a target point according to an emission situation and a composition characteristic of the atmospheric heavy metal at the target point; sampling a typical emission source of the atmospheric heavy metal at the target point, and apportioning an obtained sample by using aerosol mass spectrometry to obtain particle size distribution and mass spectra information of each particle containing heavy metals in the typical emission source of the heavy metal at the target point; establishing a source spectrum database for the typical emission source of the atmospheric heavy metal at the target point, including the particle size distribution and mass spectra information of each particle containing heavy metals;

(2) monitoring, by an aerosol mass spectrometer, the atmosphere at a to-be-monitored point on line, to obtain a number concentration, a mixing state, particle diameter distribution and a mass spectral characteristic of each particle in the atmosphere at the to-be-monitored point; classifying, by the aerosol mass spectrometer, particles in the atmosphere at the to-be-monitored point into n categories by using an adaptive resonance theory based artificial neural network (ART-2a) method based on online monitoring data of each particle; then identifying a specific category of the n categories of particles based on an element tracer method, to obtain the specific category of the n categories of particles;

(3) simultaneously measuring, by an X-ray fluorescence spectrometer, a mass concentration of each particle containing heavy metals in the atmosphere at the to-be-monitored point; setting a mass concentration emission limit for each particle containing heavy metals on the X-ray fluorescence spectrometer, and when the X-ray fluorescence spectrometer detects that the mass concentration of a certain particle containing heavy metals exceeds the emission limit, transmitting the information of the particle containing heavy metals to the aerosol mass spectrometer; and (4) matching, by the aerosol mass spectrometer, the information transmitted by the X-ray fluorescence spectrometer with a specific category of the n categories of particles to form a tracing target; obtaining a source apportionment result of the tracing target in the atmosphere at the to-be-monitored point by using a similarity algorithm based on online monitoring data of the tracing target obtained by the aerosol mass spectrometer and the source spectrum database.

Preferably, the mass spectra information of the particle containing heavy metals includes a signal intensity of a characteristic ion and a ratio between signal intensities of characteristic ions.

Preferably, the mass concentration emission limit of each particle containing heavy metals is set according to a national standard, a local standard, an industry standard, or an actual need.

Preferably, the ART-2a method inputs mass spectra data of each particle and outputs the category of each particle; the core of the ART-2a method is the dynamic formation of a weight matrix, WM (m×k), where m is an input vector, that is, the length of each mass spectra data, and k is the number of input vectors; each row of the weight matrix is called a weight vector, and each weight vector corresponds to a cluster center of a category to represent the category; specifically:

(1) randomly selecting an input vector $v_i$ from a data matrix D;

$$Si = \frac{v_i}{\|v_i\|};$$

(2) standardizing the input vector;

(3) calculating a dot product of the input vector and the existing weight matrix; if the current weight matrix is empty, that is, the current vector is a first selected vector, randomly selecting another vector as the weight vector; $P_i = S_i * WM$ (m*k);

(4) if a calculation result in (3) is larger than a preset similarity coefficient, modifying the existing weight matrix towards the current input vector; otherwise, if the calculation result is smaller than the set similarity coefficient, establishing a new category; and (5) repeating the above steps for all particles until a termination condition is reached.

Preferably, the element tracer method includes the following steps: calculating a molecular weight of a target substance, writing a tracing command, and retrieving the molecular weight of the target substance in a classification result of ART-2a, to obtain a specific category of the n categories of particles.

Preferably, the similarity algorithm includes: forming an n-dimensional characteristic vector by a mass spectral characteristic of each tracing target particle in the online monitoring data obtained by an aerosol chromatograph from a minimum mass-to-charge ratio to a maximum mass-to-charge ratio, with an interval of 1 m/z, each mass-to-charge ratio taking a mass spectra intensity signal thereof, and the mass spectra intensity signal being a peak area, a relative peak area or a peak height; adding the particle size information of the tracing target particle on the basis of the mass spectral characteristic to form an (n+1)-dimensional characteristic vector; processing each pollution source in the source spectrum database the same to form an (n+1)-dimensional characteristic vector; calculating a dot product of a multi-dimensional characteristic vector of the tracing target obtained from the online monitoring data perform and each multi-dimensional characteristic vector of the source spectrum database, and taking the maximum value of the dot product obtained after the calculation; when the maximum value is greater than a set threshold, indicating that the tracing target has a high similarity with the information in the source spectrum database, and classifying the particle into a corresponding source category of the source spectrum database; when the maximum value is less than the set threshold, marking the particle as others.

Preferably, the threshold is 0.8-0.9.

The present disclosure provides an online monitoring and source apportionment method for atmospheric fine particles containing heavy metals, including the following steps: (1) determining a typical emission source of an atmospheric heavy metal at a target point according to an emission situation and a composition characteristic of the atmospheric heavy metal at the target point; sampling a typical emission source of the atmospheric heavy metal at the target point, and apportioning an obtained sample by using aerosol mass spectrometry to obtain particle size distribution and mass spectra information of each particle containing heavy metals in the typical emission source of the heavy metal at the target point; establishing a source spectrum database for the typical emission source of the atmospheric heavy metal at the target point including the particle size distribution and mass spectra information of each particle containing heavy metals; (2) monitoring, by an aerosol mass spectrometer, the atmosphere at a to-be-monitored point on line, to obtain a number concentration, a mixing state, particle size distribution and a mass spectral characteristic of each particle in the atmosphere at the to-be-monitored point; classifying, by the aerosol mass spectrometer, particles in the atmosphere at the to-be-monitored point into n categories by using an adaptive resonance theory based artificial neural network (ART-2a) method based on online monitoring data of each particle; then identifying a specific category of the n categories of particles based on an element tracer method, to obtain the specific category of the n categories of particles; (3) simultaneously measuring, by an X-ray fluorescence spectrometer, a mass concentration of each particle containing heavy metals in the atmosphere at the to-be-monitored point; setting a mass concentration emission limit for each particle containing heavy metals on the X-ray fluorescence spectrometer, and when the X-ray fluorescence spectrometer detects that the mass concentration of a certain particle containing heavy metals exceeds the emission limit, transmitting the information of the particle containing heavy metals to the aerosol mass spectrometer; (4) matching, by the aerosol mass spectrometer, the information transmitted by the X-ray fluorescence spectrometer with a specific category of the n categories of particles to form a tracing target; obtaining a source apportionment result of the tracing target in the atmosphere at the to-be-monitored point by using a similarity algorithm based on online monitoring data of the tracing target obtained by the aerosol mass spectrometer and the source spectrum database.

The method of the present disclosure combines the aerosol mass spectrometer and the X-ray fluorescence spectrometer to quickly apportion the content, time variation trend, chemical composition, and mixing state of a heavy metal particulate in the atmosphere at the to-be-monitored point from both qualitative and quantitative perspectives, and incorporates a heavy metal-containing particle mass concentration limit system into the X-ray fluorescence spectrometer; once the mass concentration of a particle containing heavy metals exceeds the standard, the aerosol mass spectrometer can immediately receive the information of the heavy metal exceeding the standard through an information transmission system, and after the aerosol mass spectrometer receives a signal regarding the heavy metal exceeding the standard, an online source tracing system is started immediately; therefore, the method can apportion a source of the heavy metal exceeding the standard in the atmosphere at the to-be-measured point more quickly and effortlessly on line, and has an important significance and a good industrial application prospect.

BRIEF DESCRIPTION OF THE DRAWINGS

FIG. 1 is a flowchart of an online monitoring and source apportionment method for atmospheric fine particles containing heavy metals according to the present disclosure.

DETAILED DESCRIPTION

The present disclosure provides an online monitoring and source apportionment method for atmospheric fine particles containing heavy metals, including the following steps:

(1) determine a typical emission source of an atmospheric heavy metal at a target point according to an emission situation and a composition characteristic of the atmospheric heavy metal at the target point; sample a typical emission source of the atmospheric heavy metal at the target point, and apportion an obtained sample by using aerosol mass spectrometry to obtain particle size distribution and mass spectra information of each particle containing heavy metals in the typical emission source of the heavy metal at the target point; establish a source spectrum database for the typical emission source of the atmospheric heavy metal at the target point including the particle size distribution and mass spectra information of each particle containing heavy metals;

(2) monitor, by an aerosol mass spectrometer, the atmosphere at a to-be-monitored point on line, to obtain a number concentration, a mixing state, particle size distribution and a mass spectral characteristic of each particle in the atmosphere at the to-be-monitored point; classify, by the aerosol mass spectrometer, particles in the atmosphere at the to-be-monitored point into n categories by using an adaptive resonance theory based artificial neural network (ART-2a) method based on online monitoring data of each particle; then identify a specific category of the n categories of particles based on an element tracer method, to obtain the specific category of the n categories of particles;

(3) simultaneously measure, by an X-ray fluorescence spectrometer, a mass concentration of each particle containing heavy metals in the atmosphere at the to-be-monitored point; set a mass concentration emission limit for each particle containing heavy metals on the X-ray fluorescence spectrometer, and when the X-ray fluorescence spectrometer detects that the mass concentration of a certain particle containing heavy metals exceeds the emission limit, transmit the information of the particle containing heavy metals to the aerosol mass spectrometer; and (4) match, by the aerosol mass spectrometer, the information transmitted by the X-ray fluorescence spectrometer with a specific category of the n categories of particles to form a tracing target; obtain a source apportionment result of the tracing target in the atmosphere at the to-be-monitored point by using a similarity algorithm based on online monitoring data of the tracing target obtained by the aerosol mass spectrometer and the source spectrum database.

The present disclosure determines a typical emission source of an atmospheric heavy metal at a target point according to an emission situation and a composition characteristic of the atmospheric heavy metal at the target point; samples a typical emission source of the atmospheric heavy metal at the target point, and apportions an obtained sample by using aerosol mass spectrometry to obtain particle size distribution and mass spectra information of each particle containing heavy metals in the typical emission source of the heavy metal at the target point; and establishes a source spectrum database for the typical emission source of the atmospheric heavy metal at the target point including the particle size distribution and mass spectra information of each particle containing heavy metals.

In the present disclosure, when determining a typical emission source of an atmospheric heavy metal at a target point, the method preferably includes considering geographical and meteorological conditions of the typical emission source of the atmospheric heavy metal at the target point. The present disclosure has no special limit on the method for sampling the typical emission source of the atmospheric metal at the target point, and a sampling method with an aerosol mass spectrometer well known to those skilled in the art may be used.

In the present disclosure, when the aerosol mass spectrometer performs a source spectrum test, an ionization energy is preferably 0.5 mJ, and a sampling length is preferably 0-500. In the present disclosure, the mass spectra information of the particle containing heavy metals preferably includes a signal intensity of a characteristic ion and a ratio between signal intensities of characteristic ions.

After the source spectrum database is established, the present disclosure monitors, by an aerosol mass spectrometer, the atmosphere at a to-be-monitored point on line, to obtain a number concentration, a mixing state, particle size distribution and a mass spectral characteristic of each particle in the atmosphere at the to-be-monitored point; classifies, by the aerosol mass spectrometer, particles in the atmosphere at the to-be-monitored point into n categories by using an adaptive resonance theory based artificial neural network (ART-2a) method based on online monitoring data of each particle; and then identifies a specific category of the n categories of particles based on an element tracer method, to obtain the specific type of the n categories of particles;

In the present disclosure, when the aerosol mass spectrometer is used for the on-line monitoring of the atmosphere at the to-be-monitored point, an ionization energy is preferably 0.5 mJ, a sampling length is preferably 0-500, and a sampling flow rate is preferably 3 L/min.

In the present disclosure, the specific step of monitoring the atmosphere at the to-be-monitored point on line by using the aerosol mass spectrometer preferably includes:

(2-1) the atmosphere at the to-be-monitored point is directly sampled by using the aerosol mass spectrometer; when the atmosphere at different to-be-monitored points is sampled in real time, each to-be-monitored point is provided with the aerosol mass spectrometer;

(2-2) the aerosol mass spectrometer is composed of a cutting head, an aerodynamic lens, a diameter measuring laser, an ionizing laser, a mass spectrometry detector, and a data acquisition system; the cutting head screens a particulate in the atmosphere at the to-be-monitored point, and a particulate with a diameter smaller than 2.5 μm is selected to enter a group of aerodynamic lenses to focus into a beam of particles;

(2-3) based on a principle that particulates of different particle sizes fly through two laser beams at different speeds, the particle size information of the particulates can be calculated after the focused particulates pass through two 532 nm diameter measuring lasers;

(2-4) after the diameter measurement, the particulates continue to fly to an ionization area, where the particulates are ionized by a 266 nm ionizing laser; the particles are chemically apportioned by a bipolar detector at a mass spectrometry detection area to obtain the chemical composition information of each detected particle; and (2-5) the data acquisition system sorts the particle size information and chemical composition information of each detected particle to obtain online monitoring data of the particle including a number concentration, a mixing state, particle size distribution and a mass spectral characteristic.

In the present disclosure, the ART-2a method inputs mass spectra data of each particle and outputs the category of each particle; the core of the ART-2a method is the dynamic formation of a weight matrix, WM (m×k), where m is an input vector, that is, the length of each mass spectra data, and k is the number of input vectors; each row of the weight matrix is called a weight vector, and each weight vector corresponds to a cluster center of a category to represent the category; specifically:

(1) randomly select an input vector $v_i$ from a data matrix D;

$$Si = \frac{v_i}{\|v_i\|};$$

(2) standardize the input vector;

(3) calculate a dot product of the input vector and the existing weight matrix; if the current weight matrix is empty, that is, the current vector is a first selected vector, randomly select another vector as the weight vector; $P_i=S_i*WM(m*k)$;

(4) if a calculation result in (3) is larger than a preset similarity coefficient, modify the existing weight matrix towards the current input vector; otherwise, if the calculation result is smaller than the set similarity coefficient, establish a new category; and (5) repeat the above steps for all particles until a termination condition is reached.

In the present disclosure, the element tracer method preferably includes the following steps: calculate a molecular weight of a target substance, write a tracing command, and retrieve the molecular weight of the target substance in a classification result of ART-2a, to obtain a specific category of the n categories of particles.

In the present disclosure, the particles in the atmosphere at the to-be-monitored point can be classified into n categories by the ART-2a method, and a specific category of the n categories of particles in the atmosphere at the to-be-monitored point can be identified by the element tracer method.

In the present disclosure, when the aerosol mass spectrometer is used to monitor the atmosphere at the to-be-monitored point on line, the X-ray fluorescence spectrometer is synchronously used to measure the mass concentration of each particle containing heavy metals in the atmosphere at the to-be-monitored point; the mass concentration emission limit of each particle containing heavy metals is set on the X-ray fluorescence spectrometer, and when the X-ray fluorescence spectrometer detects that the mass concentration of a certain particle containing heavy metals exceeds the emission limit, the information of the particle containing heavy metals is transmitted to the aerosol mass spectrometer.

In the present disclosure, when the X-ray fluorescence spectrometer is used to determine the mass concentration of each particle containing heavy metals in the atmosphere at the to-be-monitored point, the parameters of the X-ray fluorescence spectrometer are preferably: a sampling apportionment time, which is preferably 10-300 min, and a sampling flow rate, which is preferably 4-16.7 L/min; the specific parameters are set based on specific conditions such as an actual concentration of a fine particulate matter ($PM_{2.5}$), an air velocity and a specific target metal particle in the atmosphere at the to-be-monitored point.

In the present disclosure, the mass concentration emission limit of each particle containing heavy metals is preferably set according to a national standard, a local standard, an industry standard, or an actual need.

In a specific embodiment of the present disclosure, referring to the ambient air quality standard (GB3095-2012), the mass concentration emission limit of cadmium is 0.005 $\mu g/m^3$, the mass concentration emission limit of mercury is 0.05 $\mu g/m^3$, and the mass concentration emission limit of other metals are 0.5 $\mu g/m^3$.

Preferably, the present disclosure further includes setting a time period on the X-ray fluorescence spectrometer to obtain the mass concentration of each particle containing heavy metals in every n time periods, that is, to obtain a change trend of the mass concentration of each particle containing heavy metals in the atmosphere at the to-be-monitored point with time. In the present disclosure, when the X-ray fluorescence spectrometer detects that one or more of particles containing heavy metals exceed the standard in every n time periods, the information of the one or more of particles containing heavy metals exceeding the standard in the time periods can be packaged and transmitted to the aerosol mass spectrometer. In a specific embodiment of the present disclosure, the present disclosure preferably includes packaging and transmitting the information of a particle containing heavy metals exceeding the standard within one day to the aerosol mass spectrometer.

In the present disclosure, the specific operation of measuring the mass concentration of each particle containing heavy metals in the atmosphere at the to-be-monitored point by the X-ray fluorescence spectrometer preferably includes the following steps:

(3-1) a particulate (coarse particulate matter ($PM_{10}$), $PM_{2.5}$, and total suspended particulates (TSP)) cutter is used to sample, and then the X-ray fluorescence spectrometer is used to detect a particle containing heavy metals in a particulate in the atmosphere at the to-be-monitored point;

(3-2) the atmosphere of the to-be-monitored point enters a sampling and apportionment module, and the particulate is enriched through a filter belt; at the same time, a sampling volume is calculated by the accumulation of a flow meter; and (3-3) after the sampling is completed, the filter belt with the particulate deposited is run to an X-ray detection position for measurement and apportionment; a ratio of a mass (Mt) measured by an atmospheric heavy metal online analyzer to the sampling volume ($V_t$) is calculated to obtain the concentration ($C_t$) in the unit of $\mu g/m^3$.

The present disclosure matches, by the aerosol mass spectrometer, the information transmitted by the X-ray fluorescence spectrometer with a specific category of the n categories of particles to form a tracing target; and obtains a source apportionment result of the tracing target in the atmosphere at the to-be-monitored point by using a similarity algorithm based on online monitoring data of the tracing target obtained by the aerosol mass spectrometer and the source spectrum database.

In the present disclosure, the similarity algorithm preferably includes: form an n-dimensional characteristic vector by a mass spectral characteristic of each tracing target particle in the online monitoring data obtained by an aerosol chromatograph from a minimum mass-to-charge ratio to a maximum mass-to-charge ratio, with an interval of 1 m/z, each mass-to-charge ratio taking a mass spectra intensity signal thereof, and the mass spectra intensity signal being a peak area, a relative peak area or a peak height; add the particle size information of the tracing target particle on the basis of the mass spectral characteristic to form an (n+1)-dimensional characteristic vector; process each pollution source in the source spectrum database the same to form an (n+1)-dimensional characteristic vector; calculate a dot product of a multi-dimensional characteristic vector of the tracing target obtained from the online monitoring data perform and each multi-dimensional characteristic vector of the source spectrum database, and take the maximum value of the dot product obtained after the calculation; when the maximum value is greater than a set threshold, indicate that the tracing target has a high similarity with the information in the source spectrum database, and classify the particle into a corresponding source category of the source spectrum database; when the maximum value is less than the set threshold, mark the particle as others.

In the present disclosure, the threshold is preferably 0.8-0.9, and is more preferably 0.85.

The present disclosure combines the aerosol mass spectrometer and the X-ray fluorescence spectrometer to quickly apportion the parameters of a heavy metal particulate in the atmosphere at the to-be-monitored point from both qualitative and quantitative perspectives. A heavy metal-containing particle mass concentration limit system is incorporated into the X-ray fluorescence spectrometer. Once the mass concentration of a particle containing heavy metals exceeds the standard, the aerosol mass spectrometer can immediately receive the information of the heavy metal exceeding the standard through an information transmission system. After the aerosol mass spectrometer receives a signal regarding the heavy metal exceeding the standard, an online source tracing system is started immediately. Therefore, the method can apportion a source of the heavy metal exceeding the standard in the atmosphere at the to-be-measured point more quickly and effortlessly on line, and has an important significance and a good industrial application prospect.

FIG. 1 is a flowchart of an online monitoring and source apportionment method for atmospheric fine particles containing heavy metals provided by the present disclosure: apportion a typical emission source of an atmospheric heavy metal at a target point by an aerosol mass spectrometer, to obtain particle size distribution and mass spectra information of particles containing heavy metals from different pollution sources at the target point, and establish a source spectrum database; monitor, by the aerosol mass spectrometer, the atmosphere at the to-be-monitored point on line, to obtain a number concentration, a mixing state, particle size distribution and a mass spectral characteristic of each particulate in the atmosphere at the to-be-monitored point; classify the particulates in the atmosphere at the to-be-monitored point into n categories by using an ART-2a method; determine a specific category of the n categories of particles in the atmosphere at the to-be-monitored point by an element tracer method; at the same time, measure, by an X-ray fluorescence spectrometer, a mass concentration of each particle containing heavy metals in the atmosphere at the target point, and set a mass concentration emission limit for each particle containing heavy metals; when the X-ray fluorescence spectrometer detects that the mass concentration of a certain particle containing heavy metals exceeds the standard, transmit the information of the particle containing heavy metals to the aerosol mass spectrometer; match, by the aerosol mass spectrometer, the information transmitted by the X-ray fluorescence spectrometer with a specific category of the n categories of particles to form a tracing target; and obtain a source apportionment result of the tracing target in the atmosphere at the to-be-monitored point by using a similarity algorithm based on online monitoring data of the tracing target obtained by the aerosol mass spectrometer and the source spectrum database.

The online monitoring and source apportionment method for atmospheric fine particles containing heavy metals provided by the present disclosure is described in detail below with reference to the embodiments, but the embodiments may not be understood as a limitation to the protection scope of the present disclosure.

Embodiment 1

An online monitoring and source apportionment method for atmospheric fine particles containing heavy metals, specifically including the following steps:

(1) consider the influence of geographical and meteorological factors, and determine a typical emission source of an atmospheric heavy metal at a target point, according to an emission situation and a composition characteristic of the atmospheric heavy metal at the target point; manually sample a typical emission source of the atmospheric heavy metal at the target point, and introduce a sample into an aerosol mass spectrometer to obtain particle size distribution and mass spectra information of each heavy metal pollution source (more than 20, for example, As, Cd, Mn, Cr, Fe, Co, Ni, Cu, Zn and Pb, etc.) at the target point; establish a source spectrum database;

(2) monitor, by the aerosol mass spectrometer, the atmosphere at the target point on line, to obtain a number concentration, particle size distribution, a mass spectral characteristic and a mixing state of each particulate in the atmosphere at the target point; specifically:

(2-1) the atmosphere at a to-be-monitored point is directly sampled by using the aerosol mass spectrometer; when the atmosphere at different to-be-monitored points is sampled in real time, each to-be-monitored point is provided with the aerosol mass spectrometer;

(2-2) the aerosol mass spectrometer is composed of a cutting head, an aerodynamic lens, a diameter measuring laser, an ionizing laser, a mass spectrometry detector, and a data acquisition system; the cutting head screens a particulate in the atmosphere at the to-be-monitored point, and a particulate with a diameter smaller than 2.5 μm is selected to enter a group of aerodynamic lenses to focus into a beam of particles;

(2-3) based on a principle that particulates of different particle sizes fly through two laser beams at different speeds, the particle size information of the particulates can be calculated after the focused particulates pass through two 532 nm diameter measuring lasers;

(2-4) after the diameter measurement, the particulates continue to fly to an ionization area, where the particulates are ionized by a 266 nm ionizing laser; the particles are chemically apportioned by a bipolar detector at a mass spectrometry detection area to obtain the chemical composition information of each detected particle; and (2-5) the data acquisition system sorts the particle size information and chemical composition information of each detected particle to obtain online monitoring data of the particle including a number concentration, a mixing state, particle size distribution and a mass spectral characteristic, where the number concentration of As is 1311 per day, the number concentration of Cd is 254 per day, the number concentration of Cr is 547 per day, the number concentration of Cu is 6853 per day, the number concentration of Pb is 3254 per day, the number concentration of Zn is 734 per day;

the particles in the atmosphere at the to-be-monitored point are classified into n categories by an ART-2a method, and then a specific category of the n categories of particles in the atmosphere at the to-be-monitored point is identified by an element tracer method;

(3) measure, by an X-ray fluorescence spectrometer, a mass concentration of a particle containing heavy metals in a particulate in the atmosphere at the target point, to obtain hourly concentrations of particles containing heavy metals, make a list for comparison, and screen out daily concentrations of the particles containing heavy metals; the specific process is:

(3-1) a particulate (coarse particulate matter ($PM_{10}$), $PM_{2.5}$, and total suspended particulates (TSP)) cutter is used to sample, and then the X-ray fluorescence spectrometer is used to detect a particle containing heavy metals in a particulate in the atmosphere at the to-be-monitored point;

(3-2) the atmosphere of the to-be-monitored point enters a sampling and apportionment module, and the particulate is enriched through a filter belt; at the same time, a sampling volume is calculated by the accumulation of a flow meter; and (3-3) after the sampling is completed, the filter belt with the particulate deposited is run to an X-ray detection position for measurement and apportionment; a ratio of a mass (Mt) measured by an atmospheric heavy metal online analyzer to the sampling volume ($V_t$) is calculated to obtain the concentration ($C_i$) in the unit of $\mu g/m^3$;

a mass concentration emission limit is set for each particle containing heavy metals, where the mass concentration emission limit of cadmium is 0.005 $\mu g/m^3$, the mass concentration emission limit of mercury is 0.05 $\mu g/m^3$, and the concentration emission limit of other metals is 0.5 $\mu g/m^3$; when the X-ray fluorescence spectrometer detects that the mass concentration of a certain particle containing heavy metals exceeds the standard, the information of the particle containing heavy metals is immediately transmitted to the aerosol mass spectrometer;

the aerosol mass spectrometer matches the information transmitted by the X-ray fluorescence spectrometer with a specific category of the n categories of particles to form a tracing target; based on online monitoring data of the tracing target obtained by the aerosol mass spectrometer and the source spectrum database, a 1000-dimensional characteristic vector is formed by mass spectra information of each tracing target particle in the online monitoring data obtained by an aerosol chromatograph from −500 m/z to +500 m/z, with an interval of 1 m/z, each mass-to-charge ratio taking a relative peak area signal thereof; the particle size information of the tracing target particle is added on the basis of the mass spectral characteristic to form a 1001-dimensional characteristic vector; each pollution source in the source spectrum database is processed the same to form a 10001-dimensional characteristic vector; a dot product of a multi-dimensional characteristic vector of the tracing target obtained from the online monitoring data and each multi-dimensional characteristic vector of the source spectrum database is calculated, and the maximum value of the dot product obtained after the calculation is taken; when the maximum value is greater than a set threshold 0.85, it is indicated that the tracing target has a high similarity with the information in the source spectrum database, and the particle is classified into a corresponding source category of the source spectrum database; when the maximum value is less than the set threshold, the particle is marked as others.

The source apportionment results of the atmospheric fine particles containing heavy metals at the to-be-monitored point are as follows:

Source composition of As: 51.1% of fuel coal, 42.5% of metal smelting, 5.9% of chemical industry, and 0.5% of others;

Source composition of Cd: 60% of construction materials, 8.6% of metal smelting, 6.1% of pharmaceuticals, and 25.3% of others;

Source composition of Cr: 17.2% of dust, 9.6% of exhaust gas, 16.9% of fuel coal, 35.7% of building materials, 13.5% of metal smelting, 2.8% of pharmaceuticals, and 4.3% of others;

Source composition of Cu: 4.3% of dust, 24.4% of fuel coal, 44.2% of building materials, 8.2% of textile printing and dyeing, 10.2% of metal smelting, and 8.7% of others;

Source composition of Pb: 47.8% of dust, 8.6% of exhaust gas, 9.9% of fuel coal, 12.9% of building materials, and 20.8% of metal smelting;

Source composition of Zn: 46.3% of metal smelting, 20.3% of pharmaceuticals, 2.6% of building materials, and 30.8% of others.

The foregoing descriptions are only preferred implementation manners of the present disclosure. It should be noted that for a person of ordinary skill in the art, several improvements and modifications may further be made without departing from the principle of the present disclosure. These improvements and modifications should also be deemed as falling within the protection scope of the present disclosure.

What is claimed is:

1. An online monitoring and source apportionment method for atmospheric fine particles containing heavy metals, comprising the following steps:

(1) determining a typical emission source of an atmospheric heavy metal at a target point according to an emission situation and a composition characteristic of the atmospheric heavy metal at the target point; sampling a typical emission source of the atmospheric heavy metal at the target point, and apportioning an obtained sample by using aerosol mass spectrometry to obtain particle size distribution and mass spectra information of each particle containing heavy metals in the typical emission source of the heavy metal at the target point; establishing a source spectrum database for the typical emission source of the atmospheric heavy metal at the target point, comprising the particle size distribution and mass spectra information of each particle containing heavy metals;

(2) monitoring, by an aerosol mass spectrometer, the atmosphere at a to-be-monitored point on line, to obtain a number concentration, a mixing state, particle size distribution and a mass spectral characteristic of each particle in the atmosphere at the to-be-monitored point; classifying, by the aerosol mass spectrometer, particles in the atmosphere at the to-be-monitored point into n categories by using an adaptive resonance theory based artificial neural network (ART-2a) method based on online monitoring data of each particle; then identifying a specific category of the n categories of particles based on an element tracer method, to obtain the specific category of the n categories of particles;

(3) simultaneously measuring, by an X-ray fluorescence spectrometer, a mass concentration of each particle containing heavy metals in the atmosphere at the to-be-monitored point; setting a mass concentration emission limit for each particle containing heavy metals on the X-ray fluorescence spectrometer, and when the X-ray fluorescence spectrometer detects that the mass concentration of a certain particle containing heavy metals exceeds the emission limit, transmitting the information of the particle containing heavy metals to the aerosol mass spectrometer; and (4) matching, by the aerosol mass spectrometer, the information transmitted by the X-ray fluorescence spectrometer with a specific category of the n categories of particles to form a tracing target; obtaining a source apportionment result of the tracing target in the atmosphere at the to-be-monitored point by using a similarity algorithm based on online monitoring data of the tracing target obtained by the aerosol mass spectrometer and the source spectrum database.

2. The method according to claim 1, wherein the mass spectra information of the particle containing heavy metals comprises a signal intensity of a characteristic ion and a ratio between signal intensities of characteristic ions.

3. The method according to claim 1, wherein the mass concentration emission limit of each particle containing heavy metals is set according to a national standard, a local standard, an industry standard, or an actual need.

4. The method according to claim 1, wherein the ART-2a method inputs mass spectra data of each particle and outputs the category of each particle; the core of the ART-2a method is the dynamic formation of a weight matrix, WM (m×k), wherein m is an input vector, that is, the length of each mass spectra data, and k is the number of input vectors; each row of the weight matrix is called a weight vector, and each weight vector corresponds to a cluster center of a category to represent the category; specifically:

(1) randomly selecting an input vector $v_i$ from a data matrix D;

(2) standardizing the input vector;

$$Si = \|v_i\|;$$

(3) calculating a dot product of the input vector and the existing weight matrix; if the current weight matrix is empty, that is, the current vector is a first selected vector, randomly selecting another vector as the weight vector; $P_i=S_i*WM(m*k)$;

(4) if a calculation result in (3) is larger than a preset similarity coefficient, modifying the existing weight matrix towards the current input vector; otherwise, if the calculation result is smaller than the set similarity coefficient, establishing a new category; and (5) repeating the above steps for all particles until a termination condition is reached.

5. The method according to claim 1, wherein the element tracer method comprises the following steps: calculating a molecular weight of a target substance, writing a tracing command, and retrieving the molecular weight of the target substance in a classification result of ART-2a, to obtain a specific category of the n categories of particles.

6. The method according to claim 1, wherein the similarity algorithm comprises: forming an n-dimensional characteristic vector by a mass spectral characteristic of each tracing target particle in the online monitoring data obtained by an aerosol chromatograph from a minimum mass-to-charge ratio to a maximum mass-to-charge ratio, with an interval of 1 m/z, each mass-to-charge ratio taking a mass spectra intensity signal thereof, and the mass spectra intensity signal being a peak area, a relative peak area or a peak height; adding the particle size information of the tracing target particle on the basis of the mass spectral characteristic to form an (n+1)-dimensional characteristic vector; processing each pollution source in the source spectrum database the same to form an (n+1)-dimensional characteristic vector; calculating a dot product of a multi-dimensional characteristic vector of the tracing target obtained from the online monitoring data perform and each multi-dimensional characteristic vector of the source spectrum database, and taking the maximum value of the dot product obtained after the calculation; when the maximum value is greater than a set threshold, indicating that the tracing target has a high similarity with the information in the source spectrum database, and classifying the particle into a corresponding source category of the source spectrum database; when the maximum value is less than the set threshold, marking the particle as others.

7. The method according to claim 6, wherein the threshold is 0.8-0.9.

* * * * *